(12) United States Patent
Gijsbers et al.

(10) Patent No.: US 11,839,509 B2
(45) Date of Patent: Dec. 12, 2023

(54) ULTRASOUND SYSTEM AND METHOD FOR INTERVENTIONAL DEVICE TRACKING AND GUIDANCE USING INFORMATION FROM NON-INVASIVE AND INVASIVE PROBES

(71) Applicant: KONINKLIJKE PHILIPS N.V., Eindhoven (NL)

(72) Inventors: Gerardus Henricus Maria Gijsbers, Liempde (NL); Alexander Franciscus Kolen, Eindhoven (NL); Harm Jan Willem Belt, Weert (NL); Nenad Mihajlovic, Eindhoven (NL); Jean-Luc Francois-Marie Robert, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 207 days.

(21) Appl. No.: 16/619,194

(22) PCT Filed: Jun. 1, 2018

(86) PCT No.: PCT/EP2018/064406
§ 371 (c)(1),
(2) Date: Dec. 4, 2019

(87) PCT Pub. No.: WO2018/224397
PCT Pub. Date: Dec. 13, 2018

(65) Prior Publication Data
US 2020/0113540 A1    Apr. 16, 2020

Related U.S. Application Data

(60) Provisional application No. 62/516,446, filed on Jun. 7, 2017.

(30) Foreign Application Priority Data

Jun. 30, 2017  (EP) .................................. 17178928

(51) Int. Cl.
*A61B 8/00*  (2006.01)
*A61B 8/08*  (2006.01)
(Continued)

(52) U.S. Cl.
CPC .......... *A61B 8/0883* (2013.01); *A61B 8/0841* (2013.01); *A61B 8/12* (2013.01);
(Continued)

(58) Field of Classification Search
CPC ....... A61B 8/0883; A61B 8/0841; A61B 8/12; A61B 8/4263; A61B 8/4477
See application file for complete search history.

(56) References Cited

U.S. PATENT DOCUMENTS 5,836,882 A * 11/1998 Frazin .................. A61B 8/0841
600/462
5,997,479 A   12/1999 Savord
(Continued)

FOREIGN PATENT DOCUMENTS

JP    2007029335 A    2/2007
JP    2016165459 A    9/2016
(Continued)

OTHER PUBLICATIONS

International Search Report & Written Opinion of PCT/EP2018/064406, dated Jul. 26, 2018.

*Primary Examiner* — Shahdeep Mohammed
*Assistant Examiner* — Amal Aly Farag (57) ABSTRACT

The present invention relates to an ultrasound system. A first non-invasive ultrasound probe receives first ultrasound data having a first field of view and a second invasive ultrasound
(Continued)

probe receives second ultrasound data having a second field of view which is different from the first field of view. A tracking unit determines tracking data including a position and orientation of the first non-invasive ultrasound probe relative to the second invasive ultrasound probe. A registration unit registers the second field of view into the first field of view based on the tracking data.

15 Claims, 3 Drawing Sheets

(51) Int. Cl.
 *A61B 8/12* (2006.01)
 *A61B 8/14* (2006.01)
(52) U.S. Cl.
 CPC .............. *A61B 8/14* (2013.01); *A61B 8/4263* (2013.01); *A61B 8/4477* (2013.01); *A61B 8/463* (2013.01); *A61B 8/466* (2013.01); *A61B 8/483* (2013.01); *A61B 8/5253* (2013.01)

(56) References Cited

U.S. PATENT DOCUMENTS

| | | | |
|---|---|---|---|
| 6,013,032 A | 1/2000 | Savord | |
| 6,283,919 B1 | 9/2001 | Roundhill | |
| 6,458,083 B1 | 10/2002 | Jago | |
| 6,530,885 B1 | 3/2003 | Entrekin | |
| 6,623,432 B2 | 9/2003 | Powers | |
| 2006/0270934 A1* | 11/2006 | Savord | G01S 7/52068 600/437 |
| 2007/0106147 A1* | 5/2007 | Altmann | A61B 8/543 600/407 |
| 2007/0167821 A1* | 7/2007 | Lee | A61B 8/12 600/463 |
| 2008/0146925 A1* | 6/2008 | Byrd | A61B 8/4427 600/438 |
| 2008/0146940 A1* | 6/2008 | Jenkins | A61B 8/4422 600/463 |
| 2009/0318756 A1 | 12/2009 | Fisher | |
| 2013/0041252 A1* | 2/2013 | Vignon | A61B 8/0841 600/443 |
| 2013/0131499 A1* | 5/2013 | Chan | A61B 8/4245 600/424 |
| 2013/0245433 A1* | 9/2013 | Deladi | A61B 34/20 600/424 |
| 2015/0182144 A1* | 7/2015 | Bharat | A61N 5/1067 600/424 |
| 2015/0320325 A1* | 11/2015 | Sheehan | A61B 5/0095 600/475 |
| 2016/0045184 A1 | 2/2016 | Courtney | |
| 2016/0078623 A1 | 3/2016 | Forzoni | |
| 2016/0287214 A1* | 10/2016 | Ralovich | G16H 50/20 |
| 2016/0324584 A1* | 11/2016 | Tahmasebi Maraghoosh | A61B 8/0841 |
| 2017/0024903 A1* | 1/2017 | Razzaque | A61B 6/5247 |
| 2017/0102854 A1 | 4/2017 | Choi | |
| 2018/0028066 A1 | 2/2018 | Urano | |

FOREIGN PATENT DOCUMENTS

| | | |
|---|---|---|
| WO | 2013024418 A1 | 2/2013 |
| WO | 2015189160 A1 | 12/2015 |
| WO | 2016088037 A1 | 6/2016 |

* cited by examiner

ULTRASOUND SYSTEM AND METHOD FOR INTERVENTIONAL DEVICE TRACKING AND GUIDANCE USING INFORMATION FROM NON-INVASIVE AND INVASIVE PROBES

FIELD OF THE INVENTION

The present invention relates to an ultrasound system, to a corresponding method, and to a computer program for carrying out said method. The system, method and computer program may be particularly, but not solely, used in the field of structural heart disease (SHD) interventions.

BACKGROUND OF THE INVENTION

A general field of implementation of the present invention is that of ultrasound imaging based medical interventions. More particularly the present invention finds application in the field of SHD interventions. Typical examples of SHD interventions are valve replacement, valve repair, transcatheter aortic-valve implantation (TAVI), treatments of ventricular septal defects, mitral clip procedures, and treatments of the left atrial appendage.

Most SHD interventions depend heavily on echography based guidance and navigation. Echography is typically supported by the use of X-ray fluoroscopy and iodine contrast due to echography's sub-optimal echo resolution and image quality and its inability to reliably image devices. X-ray is used in-part to obtain an overview of the region of interest, and in-part to image the different interventional devices and track their positions. In order to reliably guide the instruments, a contrast agent is frequently used.

The disadvantages of this approach include the accumulation of X-ray dose and contrast-induced kidney damage. Therefore, there is a need to limit the use of fluoroscopic guidance to reduce X-ray dose and iodine contrast use.

WO 2016/088037 A1 discloses an ultrasound probe that uses optical shape sensing for tracking the position and orientation of the ultrasound probe. Ultrasound probe navigation is facilitated by the position and orientation information delivered by the optical shape sensing device.

WO2015189160A1 relates to a medical image processing device that receives a first and a second medical image of an anatomical object of interest. Each of the first and the second medical images comprises a different field of view, and the first medical image and the second medical image show a same or similar anatomical state of the anatomical object of interest. A registration unit determines a transformation from an image space of the second medical image to an image space of the first medical image. A transformation unit transforms the second medical image into the image space of the first medical image based on said transformation. A segmentation unit performs an overall segmentation that makes use of both the first medical image and the transformed second medical image without fusing the first medical image and the transformed second medical image.

SUMMARY OF THE INVENTION

It is an object of the present invention to provide an ultrasound system and method which offer improved soft tissue navigation. Further objects of the invention include the provision of a safe and a reliable alternative to existing procedures.

In a first aspect of the present invention an ultrasound system is provided which comprises:

a first non-invasive ultrasound probe configured to acquire first ultrasound data having a first field of view;
a second invasive ultrasound probe configured to acquire second ultrasound data having a second field of view which is different from the first field of view;
a tracking unit configured to determine tracking data comprising a position and orientation of the first non-invasive ultrasound probe relative to the second invasive ultrasound probe; and
a registration unit configured to register the second field of view into the first field of view based on the tracking data.

In a second aspect of the present invention a method is presented which comprises the following steps:

receiving, from a first non-invasive ultrasound probe, first ultrasound data having a first field of view;
receiving, from a second invasive ultrasound probe, second ultrasound data having a second field of view which is different from the first field of view;
receiving tracking data comprising a position and orientation of the first non-invasive ultrasound probe relative to the second invasive ultrasound probe; and
registering the second field of view into the first field of view based on the tracking data.

In a further aspect of the present invention a computer program is presented which comprises program code means for causing a computer to carry out the steps of the above-mentioned method when said computer program is carried out on a computer.

Preferred embodiments of the invention are defined in the dependent claims. It shall be understood that the claimed method and the claimed computer program have similar and/or identical preferred embodiments as the claimed system and as defined in the dependent claims.

The present invention is based on the idea of using two or more ultrasound probes, wherein the pose (i.e. the position and orientation) of each ultrasound probe is tracked in order to determine their pose relative to one another, and wherein this tracking information is used for registering the ultrasound data acquired by one of the ultrasound probes to the ultrasound data acquired by the other one of the ultrasound probes.

The first one of the ultrasound probes is realized as a non-invasive ultrasound probe which is used outside the body. The second one of the ultrasound probes is realized as an invasive ultrasound probe which is introduced into the body. This combination of two tracked ultrasound probes enables a simplified interventional navigation and navigation of surgical instruments, particularly during SHD interventions, wherein no additional X-ray fluoroscopy or contrast agent introduction are required needed for the navigation.

The first ultrasound probe may create overview images that are used as a roadmap for planning the medical intervention, and the second ultrasound probe may deliver high resolution real-time images of the interventional target region. A radiologist may thus easily track the surgical instruments towards and into the target area in real-time without fluoroscopy.

Since the second field of view provided by the second ultrasound probe is registered into the first field of view provided by the first ultrasound probe, an easily comprehensible image may be generated that comprises both information, the overall point of view and the detailed point of view.

Since the echographic imaging may be tracked and visualized in the proper patient orientation, as with today's fluoroscopic imaging, the presented system and method provide adequate visualization and navigation without fluoroscopy.

Besides tracking the poses of the two ultrasound probes, it is furthermore preferable that ultrasound system comprises also a tracking unit for tracking an in-body interventional instrument. Thus, also the interventional instrument is tracked, preferably relative to the two ultrasound probes. This enables even better navigation during a surgery.

The herein presented ultrasound system is denoted as a "system", since it may comprises several independent devices.

For example, the system may comprise two separate ultrasound devices, one driving and computing the images of the first ultrasound probe and the other driving and computing the images of the second ultrasound probe. Both ultrasound devices are in this case preferably synchronized and connected together via the tracking unit that may be hardware- and/or software-implemented.

In another example, both ultrasound probes are steered and their data are computed by one and the same ultrasound device. Even the whole presented ultrasound system may be implemented in a single common device.

According to a preferred embodiment the first field of view of the first non-invasive ultrasound probe is larger than the second field of view of the second invasive ultrasound probe. It is furthermore preferred that a resolution of the second invasive ultrasound probe is higher than a resolution of the first non-invasive ultrasound probe.

This enables combining a large roadmap acquired by the first non-invasive ultrasound probe, which roadmap may be used for the overview planning, combined with a detailed visualization of the interventional target region acquired by the second invasive ultrasound probe.

According to an embodiment, the first non-invasive ultrasound probe is a transthoracic echocardiography (TTE) probe, and the second invasive ultrasound probe is a transesophageal echocardiography (TEE) probe or an intracardiac echocardiography (ICE) probe.

The TTE probe may be used for creating a 3D overview roadmap of the full heart and may be also used to image anatomy in areas where TEE or ICE imaging is shielded by e.g. calcifications or devices. The TEE probe or the ICE probe may be used for detailed visualization of the interventional target region, such as the aortic valve, the mitral valve, or the left atrial appendage.

While it is generally possible to use 2D ultrasound probes, it is preferred to use a 3D TTE probe as well as a 3D TEE probe or a 3D ICE probe.

It shall be noted that the ultrasound data provided by the first non-invasive ultrasound probe (e.g. the TTE probe) may, but do not necessarily have to be provided in a live mode. The first ultrasound data used for creating the overview roadmap may also be acquired beforehand, e.g. before starting the medical intervention. The 2D or 3D roadmap may be generated, for example, based on several scans in order to get a complete image data set that shows all parts of the heart. The second ultrasound data acquired by the second invasive ultrasound probe (e.g. the TEE probe or the ICE probe) are on the other hand preferably provided in a live mode in order to get live images of the region of interest.

According to a further embodiment, the ultrasound system further comprises an imaging unit which is configured to generate an ultrasound image in which a first image having the first field of view and being produced based on the first ultrasound data is overlaid with a second image having the second field of view and being produced based on the second ultrasound data.

In other words, the detailed image which is generated by the second invasive ultrasound probe and shows the comparatively smaller interventional target region in high resolution is overlaid over the overview image that is generated based on the ultrasound data provided by the first non-invasive ultrasound probe. Since both field of views are registered into a common space/coordinate system, an easily comprehensible graphical user interface may be established for the radiologist.

In a further embodiment the ultrasound system may furthermore comprise a transparency unit which enables a user of the ultrasound system to adapt a transparency of the second image.

This allows the radiologist to adapt the composite image, in which the first image is overlaid with the second image, according to his personal needs. Depending on the situation the radiologist may thus easily switch between looking at the first overview image and looking at the second detailed image in the interventional target region.

In an embodiment of the present invention, the tracking unit comprises a first tracking device configured to track a position and orientation of the first non-invasive ultrasound probe and a second tracking device configured to track a position and orientation of the second invasive ultrasound probe. In an alternative embodiment, the tracking sensor comprises a common tracking sensor configured to track a position and orientation of the first non-invasive ultrasound probe and a position and orientation of the second invasive ultrasound probe.

The second of the above-mentioned two alternative embodiments is, of course, the less cost-intensive one, since only one tracking device is needed for tracking both ultrasound probes. It is therefore the preferred embodiment.

It shall be furthermore noted that, independent of whether two separate or a common tracking device is used, it is not mandatory, even though preferred, to track the absolute positions and orientations of both ultrasound probes, as long as their position and orientation relative to one another may be determined.

In a further preferred embodiment, the tracking unit comprises a terminal to which each of the first non-invasive ultrasound probe and the second invasive ultrasound probe is releasably connected.

Both ultrasound probes may thus be realized as disposable probes that are intended to be used only once. After using them, they may be simply disconnected from the tracking unit and disposed.

According to an embodiment, the tracking unit comprises a fiber optic shape sensor.

The principle of optical shape sensing which is used in such fiber optic shape sensors relies on the usage of light information along a multicore optical fiber. One principle involved makes use of distributed strain measurement in the optical fiber using characteristic Rayleigh backscatter of controlled grating patterns. The shape along the optical fiber begins at a specific point along the sensor, known as the launch point, and the subsequent shape position and orientation are relative to that point. For meaningful clinical use, shape-sensed devices need to be registered to an imaging frame of reference. Such a fiber optic shape sensor may then be easily used for device localization and navigation during medical interventions.

In a preferred embodiment of the present invention, the fiber optic shape sensor comprises an optical fiber which connects the first non-invasive ultrasound probe with the second invasive ultrasound probe.

The relative pose of the two ultrasound probes may thus be easily determined by means of a common tracking sensor having only one common optical fiber. While the usage of only one optical fiber is preferred, each ultrasound probe may also be tracked by a separate optical fiber, as already mentioned above. In this case both optical fibers/tracking devices need to be calibrated and referenced to one another.

In an alternative embodiment the tracking unit comprises an electromagnetic localization sensor. In a still further alternative embodiment, the tracking unit may also comprise an optical sensor, such as a camera, for tracking the position of the first non-invasive ultrasound probe.

BRIEF DESCRIPTION OF THE DRAWINGS

These and other aspects of the invention will be apparent from and elucidated with reference to the embodiments described hereinafter. In the following drawings

FIG. 3 schematically shows a process for forming an image according to an embodiment of the present invention, wherein

DETAILED DESCRIPTION OF THE INVENTION

Figure 1:
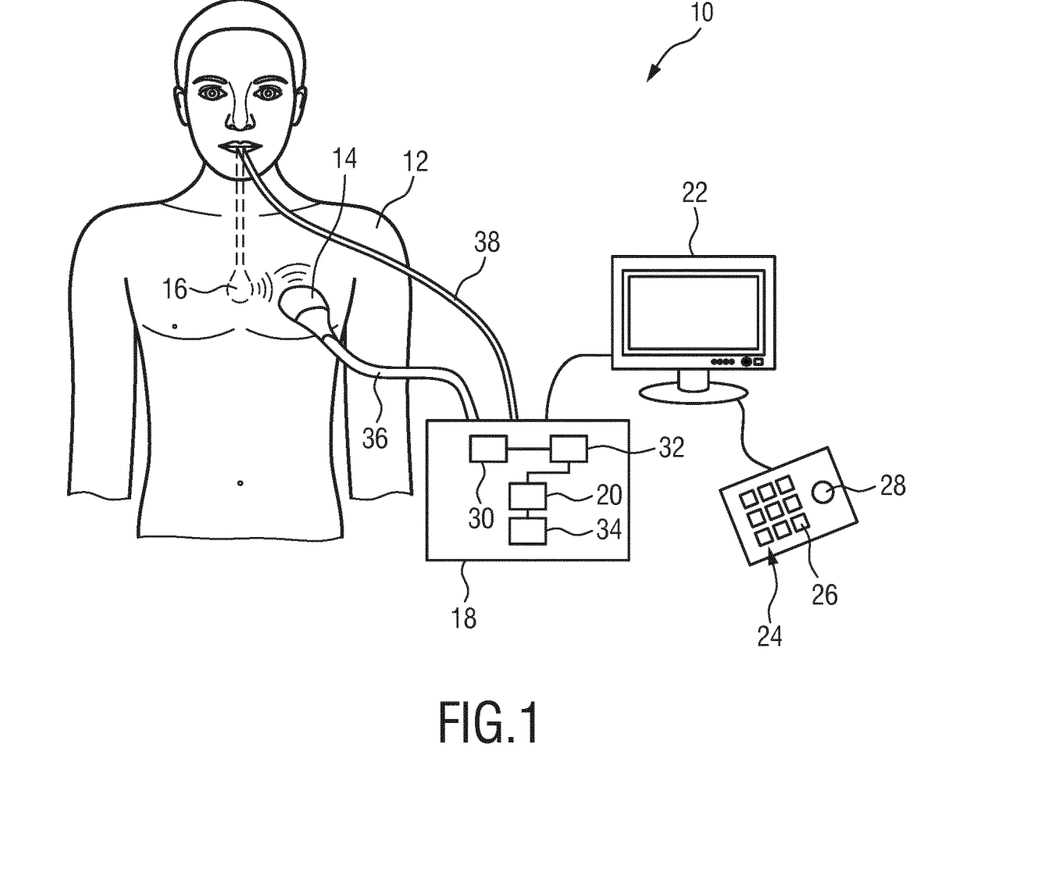
FIG. 1 shows a schematic representation of an exemplary embodiment of an ultrasound system according to the present invention in use.

FIG. 1 shows a schematic illustration of an ultrasound system according to an embodiment of the present invention. The ultrasound system is in its entirety denoted by reference numeral 10. The ultrasound system 10 is applied to inspect a volume of an anatomical site, in particular an anatomical site of a patient 12, in particular a region of the heart of the patient 12.

The ultrasound system 10 comprises two ultrasound probes 14, 16. The first ultrasound probe 14 is realized as a non-invasive ultrasound probe. The second ultrasound probe 16 is realized as an invasive ultrasound probe.

In the example illustrated in FIG. 1 the first ultrasound probe 14 is realized as a TTE probe, and the second ultrasound probe 16 is realized as a TEE probe. During a SHD intervention the first ultrasound probe 14 would be typically placed and moved over the chest of the patient 12, while the second ultrasound probe 16 is in this exemplary case typically introduced through the esophagus.

The second ultrasound probe 16 may alternatively be realized as an ICE probe that is introduced in the manner of a catheter directly into the heart of the patient 12. Both ultrasound probes 14, 16 are preferably configured to deliver 3D ultrasound data. Each of the two ultrasound probes 14, 16 has at least one transducer array comprising a multitude of transducer elements for transmitting and/or receiving ultrasound waves. The transducer elements are preferably arranged in a two-dimensional array, in particular for providing a multi-planar or three-dimensional image.

An example for the first ultrasound probe 14 is the X5-1 transducer sold by the applicant. An example for the second ultrasound probe 16 is the X8-2t transducer sold by the applicant. However, it is to be noted that this is only one of multiple examples for ultrasound probes that may be used according to the present invention.

Figure 2:
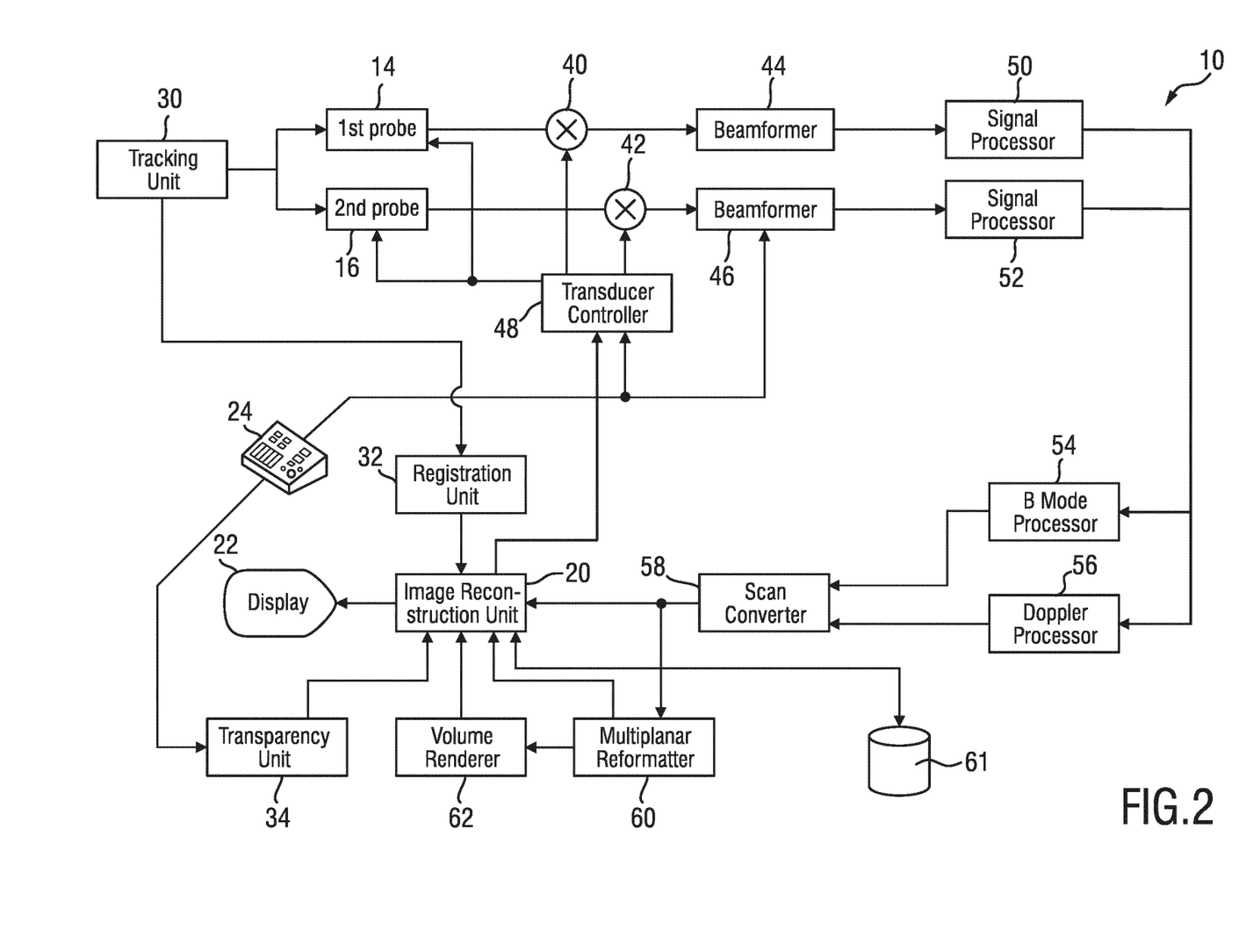
FIG. 2 shows a schematic block diagram of an embodiment of the ultrasound system according to the present invention.

The ultrasound system 10 further comprises a computation unit 18 including an image reconstruction unit 20. The image reconstruction unit 20 controls the generation and provision of the ultrasound image based on the data acquired by the ultrasound probes 14 and 16. As will be explained in detail further below, the image reconstruction unit 20 may control not only the acquisition of data via the transducer arrays of the ultrasound probes 14, 16, but also signal and image processing that form a 2D or 3D image sequence out of the echoes of the ultrasound beams received by the transducer arrays of the ultrasound probes 14, 16. Even though only one computation unit 18 and only one image reconstruction unit 20 are shown in FIG. 2, the system 10 may comprises a plurality of computation units 18 and image reconstruction units 20.

A particular example that may be used as image reconstruction unit 20 is the Philips EPIQ device, which could be applied in conjunction with the present invention.

In an exemplary implementation, the herein presented system may comprise two synchronized EPIQ devices as two separate image reconstruction units 20, one driving the TTE probe 14 and the other one driving the TEE or ICE probe 16. In an alternative implementation, a single EPIQ device or other ultrasound device is used as single image reconstruction unit 20 and allows for driving both ultrasound probes 14, 16 simultaneously.

The ultrasound system 10 further comprises a display 22 for displaying the generated ultrasound images to the user. Still further, an input device 24 may be provided that enables a user to steer the system 10 and control its settings. The input device 24 may exemplarily comprise a keyboard 26 and further inputting devices, such as a track ball 28 or a mouse. The input device 24 may be connected to the display 22 or directly to the computation unit 18.

Besides the image reconstruction unit 20, the computation unit 18 preferably further comprises a tracking unit 30 and a registration unit 32. Optionally, the computation unit 18 may further comprise a transparency unit 34. The tracking unit 30 is configured to determine tracking data comprising a position and orientation of the first non-invasive ultrasound probe 14 relative to the second invasive ultrasound probe 16. The registration unit 32 is configured to register the ultrasound image data provided by the second ultrasound probe 16 into the same imaging space as the first ultrasound image data provided by the first ultrasound probe 14. This registration is based on the tracking data provided by the tracking unit 30. The function of the optional transparency unit 34 will be elucidated in detail further below.

It shall be noted that the above-mentioned units 20, 30, 32, and 34 may be software and/or hardware implemented. It shall be also noted that these units are indicated as separate units only for illustration purposes. In practice, they may be realized as separate structural units. However, they may also be implemented in one and the same unit.

Before referring to the functional details of the present invention including the functions of units 20, 30, 32, and 34 some basic principles of forming an ultrasound image in the ultrasound system 10 shall be explained with reference to the schematic block diagram illustrated in FIG. 2.

Each of the two ultrasound probes 14, 16 may, for example, comprise a CMUT transducer array. The transducer array may alternatively comprise piezoelectric transducer elements formed of materials such as PZT or PVDF.

The transducer arrays are preferably one- or two-dimensional arrays of transducer elements capable of scanning in three dimensions for 3D imaging. Each of the two ultrasound probes 14, 16 furthermore preferably comprises a microbeamformer which controls transmission and reception of signals by the CMUT array cells or piezoelectric elements. Microbeamformers are capable of at least partial beamforming of the signal received by groups or "patches" of transducer elements as described in U.S. Pat. Nos. 5,997, 479, 6,013,032, and 6,623,432.

Each of the ultrasound probes 14, 16 are preferably coupled by probe cable 36, 38 (see FIG. 1) to the computation unit 18. The probe cable 36, 38 typically connects the microbeamformers of each of the ultrasound probes 14, 16 to a transmit/receive (T/R) switch 40, 42 which switches between transmission and reception and protects the main beamformers 44, 46 from high energy transmit signals when the microbeamformers are not used and the transducer arrays of the transducer probes 14, 16 are operated directly by the microbeamformers 44, 46. The transmission of ultrasonic beams under control of the microbeamformers 44, 46 is typically directed by a transducer controller 48 that is coupled to the T/R switches 40, 42 and which receives input from the users operation of the user interface or control panel 24. For simplicity reasons only one transducer controller 48 is shown in FIG. 2. However, generally also two transducer controllers may be provided, one for controlling each ultrasound probe 14, 16. One of the functions controlled by the transducer controller 48 is typically the direction in which beams are steered and focused. Beams may be steered straight ahead from (orthogonal to) the transducer array, or at different angles for wider field of view.

The partially beamformed signals produced by the microbeamformers of each ultrasound probe 14, 16 are transferred to the main beamformers 44, 46 where partially beamformed signals from individual patches of transducer elements are combined into a fully beamformed signal. For example, the main beamformers 44, 46 may each have 128 channels, each of which receives a partially beamformed signal from a patch of dozens or hundreds of CMUT transducer cells or piezoelectric elements. In this way, the signals received by thousands of transducer elements can contribute efficiently to a single beamformed signal.

The beamformed signals are transferred to signal processors 50, 52. The signal processors 50, 52 can process the received echosignals in various ways, such as bandpass filtering, decimation, I and Q component separation, and harmonic signal separation which acts to separate linear and non-linear signals so as to enable the identification of non-linear (higher harmonics of the fundamental frequency) echosignals returned from tissue and/or microbubbles comprised in a contrast agent that has been pre-administered to the body of the patient 12. The signal processors 50, 52 may also perform additional signal enhancement, such as speckle reduction, signal compounding, and noise elimination.

The process signals may be transferred to a B-mode processor 54 and a Doppler processor 56. The B-mode processor 54 employs detection of an amplitude of the received ultrasound signals for the imaging of structures in the body such as the tissue of organs and vessels in the body. B-mode images of structure of the body may be formed in either the harmonic image mode or the fundamental image mode or a combination of both, as described in U.S. Pat. Nos. 6,283,919 and 6,458,083. The Doppler processor 56 may process temporally distinct signals from tissue movement and blood flow for the detection of the motion of substances such as the flow of blood cells in the image field.

For simplicity reasons only one B-mode processor 54 and only one Doppler processor 56 is shown in FIG. 2. However, there may be two B-mode processors 54 and two Doppler processors 56, one for each ultrasound probe 14, 16. The same applies for all further units that are explained in the following.

The structural and motion signals produced by the B-mode and Doppler processors 54, 56 are then transferred to a scan converter 58 and a multiplanar reformatter 60. The scan converter arranges the echosignals in the spatial relationship from which they were received in a desired image format. For instance, the scan converter 58 may arrange the echosignals into 2D sector-shaped formats, or 3D pyramidal images. The scan converter 58 can overlay a B-mode structural image with colors corresponding to motion at points in the image field with their Doppler-estimated velocities to produce a color Doppler image which depicts the motion of tissue and blood flow in the image field. The multiplanar reformatter 60 converts echoes which are received from points in a common plane in a volumetric region of the body into an ultrasonic image of that plane, as described in U.S. Pat. No. 6,443,896.

A volume renderer 62 may convert the echosignals of a 3D dataset into a projected 3D image sequence over time as viewed from a given reference point, as this is described in U.S. Pat. No. 6,530,885. The 3D image sequence is transferred from the scan converter 58, the multiplanar reformatter 60, and the volume renderer 62 to the image reconstruction unit 20 for further enhancement, buffering, temporary storage and/or for display on the display 22. The user interface 24 may also be coupled to the multiplanar reformatter 60 for selection and control of the planes of multiplanar reformatted (MPR) images which may be used to perform quantified measures in the image field of the MPR images. The data and images may be saved in a database 61.

Again, it shall be noted that the afore-mentioned ultrasound system 10 has only been explained as one possible example for an application of the herein presented system. It shall be noted that the herein presented ultrasound system 10 does not have to comprise all of the components explained before. On the other hand, the ultrasound system 10 according to the present invention may comprise further components, if necessary. Still further, it shall be noted that a plurality of the afore-mentioned components do not necessarily have to be realized as hardware, but may also be realized as software components. A plurality of the afore-mentioned components may also be comprised in common entities or even in one single entity and do not all have to be realized as separate entities, as this is schematically shown in FIG. 2.

In a practical example, two separate ultrasound imaging devices could be included in system 10 (rather than as shown in FIG. 2), one for computing the images of each of the two ultrasound probes 14, 16. Each of the two imaging devices would include the above-mentioned units 44, 50, 54, 56, 56, 60, 62 and 20.

Figure 3A:
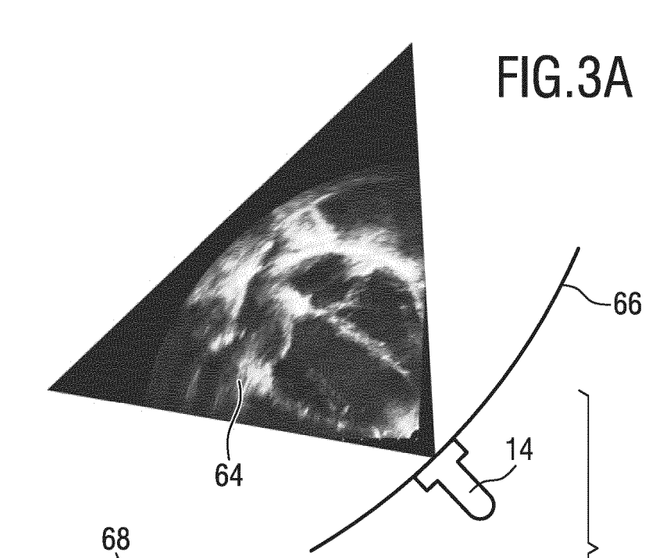
FIG. 3A illustrates imaging with a first ultrasound probe.
Figure 3B:
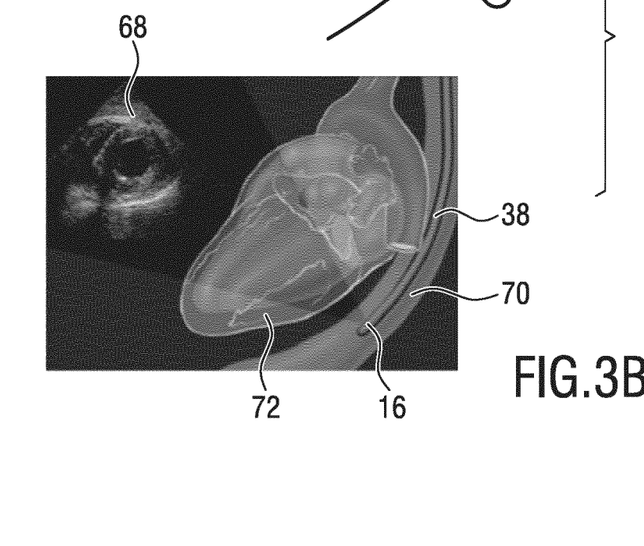
FIG. 3B illustrates imaging with a second ultrasound probe.
Figure 3C:
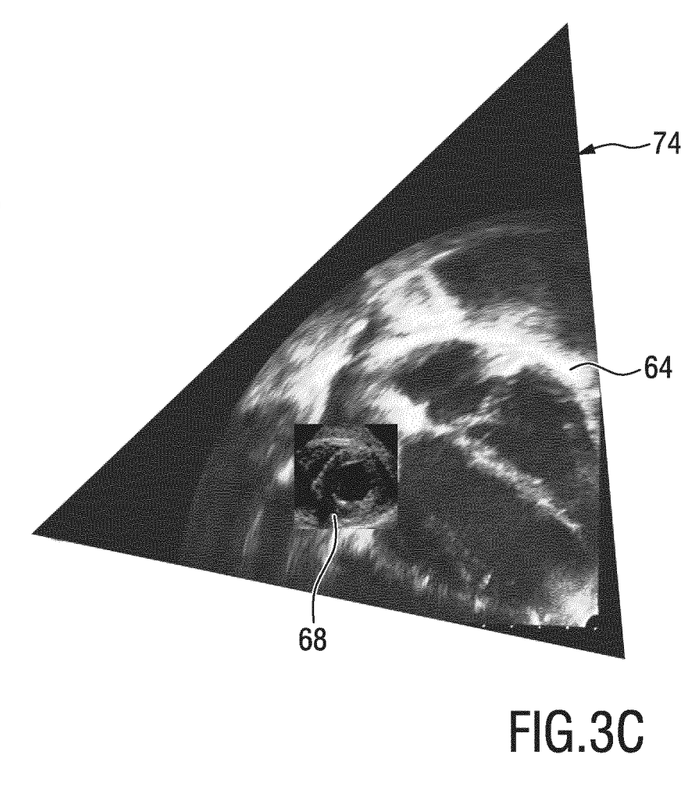
FIG. 3C illustrates an exemplary final image generated by means of the system and method according to the present invention.

FIGS. 3A-3C schematically illustrate an image-forming process according to the present invention. FIG. 3A schematically illustrates a first ultrasound image 64 which is produced based on the first ultrasound data provided by means of the first non-invasive ultrasound probe 14. The ultrasound probe 14, e.g. a TTE probe, is thereto exemplarily positioned on the chest 66 of the patient 12 in order to provide an image of the heart of the patient 12. This first image 64 may either be generated in a live mode or beforehand, i.e. before planning the medical intervention. It may be used as an overview image which preferably shows all parts of the heart. It shall be noted that the first image 64 may be generated based on several scans. The first image 64 may be a 2D or a 3D image.

FIG. 3B shows the generation of a second image 68 which is produced based on the second ultrasound data provided by the second invasive ultrasound probe 16. The second ultrasound probe 16 is in this example realized as a TEE probe which is introduced into the esophagus 70 of the patient 12 in order to provide detail images of parts of the heart 72 of the patient 12. As already explained above, the second invasive ultrasound probe 16 may alternatively be realized as an ICE probe that is introduced directly into the heart 72 of the patient 12.

While the first image 64 provides an overview of the heart 72 of the patient 12, the second image 68 provides a detail image of the heart 72 of the patient 12. The field of view of the first ultrasound probe 14 is therefore preferably larger than the field of view of the second ultrasound probe 16.

FIG. 3C illustrates a joint image 74 which is formed based on both images 64, 68. Thereto, both images 64, 68 are registered into the same imaging space, and the second image 68 is afterwards overlaid over the first image 64. In order to be enable to register both images 64, 68 into the same imaging space, the pose of both ultrasound probes 14, 16 is tracked. This means that either their positions and orientations are tracked relative to one another or their absolute positions and orientations are tracked.

The tracking unit 30 for tracking the poses of the two ultrasound probes 14, 16 is preferably realized as an optical shape sensing sensor. It may include one or more optical fibers that are comprised in the probe cables 36, 38 connecting the ultrasound probes 14, 16 to the computation unit 18. It shall be noted that the tracking unit 30 does not necessarily have to be included in the same housing as the remaining units 20, 32, and 34 of the computation unit 18. It is also conceivable that one and the same optical fiber connects the two ultrasound probes 14, 16 with each other. It shall be also noted that, instead of one common tracking sensor, the position of each ultrasound probe 14, 16 may be tracked by means of a separate sensor.

As an alternative to a fiber optic shape sensor, an electromagnetic localization sensor may also be used for tracking the position and orientation of the first and the second ultrasound probes 14, 16. The position of the non-invasive first ultrasound probe may generally also be tracked by an optical sensor, such as a camera.

The tracking information provided by the tracking unit 30 may in any way used in the registration unit 32 for registering the first and the second ultrasound images 64, 68 into the same image space, so that the image reconstruction unit 20 may finally generate the joint image 74. The optional transparency unit 34 may be used to allow the user to control the transparency of the second image 68. For example, if some of the heart structures are not visible in the second image 68, the user may increase the transparency of the second image 68 in order to observe said structures in the underlying first image 64.

The present invention thus provides a system and method using two ultrasound probes 14, 16, wherein the first ultrasound probe 14 is a non-invasive ultrasound probe that creates an intervention roadmap, and wherein the second ultrasound probe 16 is an invasive ultrasound probe which provides a high resolution real-time image of the interventional target region. The presented system and method therefore allow a radiation-free ultrasound-based navigation of SHD interventional devices.

It shall be noted that the interventional devices/surgical instruments are for simplicity reasons not shown in the drawings. However, it is preferred that also the position and orientation of the used surgical instrument, such as a catheter, is tracked. The position and orientation of the used surgical instrument may, for example, be tracked by means of an optical shape sensing system. In this way, the physician may be give a feedback about the absolute position and orientation of the used surgical instrument and/or about the position and orientation of the used surgical instrument relative to the two ultrasound probes 14, 16.

Also not shown are manipulation devices that may be optionally used to manipulate the orientation and position of the ultrasound probes 14, 16 in order to facilitate the handling for the radiologist. One or both probes 14, 16 may, for example, be steered by means of a remote-controlled movement actuator instead of moving them by hand.

It shall be also noted that the presented system and method may also be used for other medical applications, not limited to heart disease interventions. It would be also conceivable to use more than two ultrasound probes that are tracked and the images of which are combined according to the principle of the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method comprising the steps of:
  receiving, from a non-invasive ultrasound probe, first ultrasound data representative of a first ultrasound image having a first view of a target region for an interventional device;
  receiving, from an invasive ultrasound probe, second ultrasound data representative of a second ultrasound image having a second view of the target region for the interventional device, wherein the second view is different from the first view, wherein the invasive ultrasound probe is separate from the interventional device, wherein the first ultrasound data is acquired simultaneously with the second ultrasound data; and
  guiding navigation of the interventional device relative to the target region, wherein guiding the navigation comprises:

forming a joint ultrasound image comprising the first view of the target region from the first ultrasound image and the second view of the target region from the second ultrasound image; and tracking the interventional device relative to the non-invasive ultrasound probe and the invasive ultrasound probe, wherein the tracking comprises a position and orientation of the non-invasive ultrasound probe and the invasive ultrasound probe received from a tracking sensor such that the tracking is associated with a coordinate system common to the non-invasive ultrasound probe and the invasive ultrasound probe.

2. The method according to claim 1, wherein the first view is larger than the second of view.

3. The method according to claim 1, wherein the first ultrasound data received from the non-invasive ultrasound probe has a resolution and wherein the second ultrasound data received from the invasive ultrasound probe has a resolution, the resolution of the second ultrasound data being higher than the resolution of the first ultrasound data.

4. The method according to claim 1, wherein the non-invasive ultrasound probe is a transthoracic echocardiography probe.

5. The method according to claim 1, wherein the invasive ultrasound probe comprises an intra-cardiac echocardiography (ICE) catheter or a transesophageal echocardiography (TEE) probe.

6. The method according to claim 1, wherein each of the first ultrasound data and the second ultrasound data are 3D ultrasound data.

7. The method according to claim 1, the first image is overlaid with the second image in the joint ultrasound image.

8. The method according to claim 7, wherein the method further comprises selecting, from a plurality of transparency settings, a transparency setting of the second image.

9. The method according to claim 1, wherein the method further comprises releasably connecting each of the non-invasive ultrasound probe and the invasive ultrasound probe to a terminal.

10. The method according to claim 1, wherein the tracking sensor comprises a fiber optic shape sensor.

11. The method according to claim 10, wherein the method further comprises connecting the invasive ultrasound probe with the non-invasive ultrasound probe via an optical fiber of the fiber optic shape sensor.

12. The method according to claim 1, wherein the tracking sensor comprises an electromagnetic localization sensor.

13. The method according to claim 1, wherein the position and the orientation of the invasive ultrasound probe corresponds to a position and orientation of the second image relative to the first image, and wherein the joint ultrasound image is formed using the position and the orientation of the second image relative to the first image to register the second image into the first image based on the tracking data.

14. The method according to claim 1, wherein guiding the navigation is performed without performing x-ray imaging or introducing contrast agent.

15. A non-transitory computer readable storage medium comprising a computer program for causing a computer to carry out the steps of the method as claimed in claim 1 when said computer program is carried out on the computer.

* * * * *